US011423761B2

(12) United States Patent
Christian et al.

(10) Patent No.: US 11,423,761 B2
(45) Date of Patent: Aug. 23, 2022

(54) CONNECTED MONITORING SYSTEM

(71) Applicant: Gentex Corporation, Zeeland, MI (US)

(72) Inventors: David E. Christian, West Olive, MI (US); Thomas S. Wright, Holland, MI (US); Brian G. Brackenbury, Grand Haven, MI (US); Steven L. Geerlings, Holland, MI (US); Darin D. Tuttle, Byron Center, MI (US); Shane M. Courbier, Grand Rapids, MI (US)

(73) Assignee: GENTEX CORPORATION, Zeeland, MI (US)

( * ) Notice: Subject to any disclaimer, the term of this patent is extended or adjusted under 35 U.S.C. 154(b) by 82 days.

(21) Appl. No.: 17/083,425

(22) Filed: Oct. 29, 2020

(65) Prior Publication Data

US 2021/0125483 A1    Apr. 29, 2021

Related U.S. Application Data

(60) Provisional application No. 62/927,261, filed on Oct. 29, 2019.

(51) Int. Cl.
*G08B 21/18* (2006.01)
*G01N 27/12* (2006.01)
(Continued)

(52) U.S. Cl.
CPC .............. *G08B 21/18* (2013.01); *A61B 5/002* (2013.01); *A61B 5/02444* (2013.01); *A61B 5/0507* (2013.01); *A61B 5/742* (2013.01); *A61B 5/7405* (2013.01); *A61B 5/748* (2013.01); *G01J 5/0018* (2013.01); *G01J 5/20* (2013.01); *G01N 27/128* (2013.01); *G01N 33/0054* (2013.01); *G07C 9/00896* (2013.01); *G08B 17/10* (2013.01); *H04R 1/028* (2013.01); *H04R 1/08* (2013.01);
(Continued)

(58) Field of Classification Search
CPC ........ G08B 21/18; G08B 17/10; A61B 5/002; A61B 5/02444; A61B 5/0507; A61B 5/7405; A61B 5/742; A61B 5/748; G01J 5/0018; G01J 5/20; G01N 27/128; G01N 33/0054; G07C 9/00896; H04R 1/028; H04R 1/08
USPC ....................................................... 340/540
See application file for complete search history.

(56) References Cited

U.S. PATENT DOCUMENTS 6,002,994 A * 12/1999 Lane .................. G08B 21/0469
                                                        702/188
8,384,513 B2    2/2013 Witkowski
(Continued)

FOREIGN PATENT DOCUMENTS

WO    2015054288 A1    4/2015

*Primary Examiner* — Kerri L Mcnally
(74) *Attorney, Agent, or Firm* — Price Heneveld LLP; Brian James Brewer

(57) ABSTRACT

A multi-zone monitoring system is disclosed. The system includes a plurality of sensor modules configured to monitor conditions in a plurality of detection zones. The sensor modules include a combination of detection devices configured to detect different conditions based on a designated zone of each sensor module. The system further includes a reporting device in communication with each of the sensor modules. The reporting device is configured to report the status of each of the detection zones based on indications communicated via the detection devices in the corresponding detection zone.

17 Claims, 6 Drawing Sheets

(51) Int. Cl.
    *G01J 5/20*     (2006.01)
    *G01J 5/00*     (2022.01)
    *A61B 5/0507*     (2021.01)
    *A61B 5/024*     (2006.01)
    *A61B 5/00*     (2006.01)
    *G07C 9/00*     (2020.01)
    *G08B 17/10*     (2006.01)
    *H04R 1/02*     (2006.01)
    *H04R 1/08*     (2006.01)
    *G01N 33/00*     (2006.01)

(52) U.S. Cl.
    CPC ....... *A61B 2503/04* (2013.01); *A61B 2505/07* (2013.01); *G01J 2005/0077* (2013.01); *G01J 2005/202* (2013.01); *G07C 2009/00928* (2013.01)

(56) References Cited

U.S. PATENT DOCUMENTS

| | | | |
|---|---|---|---|
| 9,819,498 B2 | 11/2017 | Vuyst et al. | |
| 9,947,312 B1* | 4/2018 | Hieb | H04N 21/41265 |
| 10,032,366 B2* | 7/2018 | Bodurka | G01S 7/003 |
| 2008/0045832 A1* | 2/2008 | McGrath | A61B 5/08 |
| | | | 600/427 |
| 2015/0302728 A1* | 10/2015 | Gettings | G08B 3/10 |
| | | | 340/506 |
| 2016/0379468 A1* | 12/2016 | Wu | H04M 1/72454 |
| | | | 340/632 |
| 2018/0158288 A1* | 6/2018 | Logan | G08B 1/08 |
| 2018/0247475 A1* | 8/2018 | Archbold | G07C 9/00182 |
| 2018/0321652 A1* | 11/2018 | Jablokov | G05B 19/042 |
| 2018/0348129 A1 | 12/2018 | Zang et al. | |
| 2019/0223659 A1* | 7/2019 | Shete | A47J 36/321 |
| 2019/0323979 A1 | 10/2019 | Cammenga et al. | |
| 2020/0080978 A1 | 3/2020 | Zang et al. | |

* cited by examiner

CONNECTED MONITORING SYSTEM

CROSS-REFERENCE TO RELATED APPLICATIONS

This application claims priority under 35 U.S.C. § 119(e) and the benefit of U.S. Provisional Application No. 62/927,261 entitled CONNECTED MONITORING SYSTEM, filed on Oct. 29, 2019, by David E. Christian et al., the entire disclosure of which is incorporated herein by reference.

TECHNOLOGICAL FIELD

The present disclosure relates generally to a monitoring system and more particularly relates to a monitoring system for a home or building.

SUMMARY

In one aspect of the disclosure, a multi-zone monitoring system is disclosed. The system comprises a plurality of sensor modules configured to monitor conditions in a plurality of detection zones. The sensor modules comprise a combination of detection devices configured to detect different conditions based on a designated zone of each sensor module. The system further comprises a reporting device in communication with each of the sensor modules. The reporting device is configured to report the status of each of the detection zones based on indications communicated via the detection devices in the corresponding detection zone.

In another aspect of the disclosure, a multi-zone monitoring system is disclosed. The system comprises a plurality of sensor modules configured to monitor conditions in a plurality of detection zones. Each of the sensor modules comprises a combination of detection devices configured to detect different conditions based on a designated zone of each sensor module. The detection devices comprise a kitchen sensor module configured to detect conditions in a kitchen region. The kitchen sensor module is configured to detect a burning food associated with a stove or cooktop. The system further comprise a reporting device in communication with each of the sensor modules. The reporting device is configured to report the status of each of the detection zones based on indications communicated via the detection devices in the corresponding detection zone.

In yet another aspect of the disclosure, a multi-zone monitoring system is disclosed and includes a plurality of sensor modules configured to monitor conditions in a plurality of detection zones. The sensor modules comprise a combination of detection devices configured to detect different conditions based on a designated zone of each sensor module. The plurality of sensor modules comprises a nursery sensor module configured to detect conditions in a nursery region. The nursery sensor module comprises an ammonia sensor configured to detect ammonia in the air of the nursery region. The system further includes a reporting device in communication with each of the sensor modules. The reporting device is configured to report the status of each of the detection zones based on indications communicated via the detection devices in the corresponding detection zone. The reporting device is configured to output a urine or excrement notification in response to the detection of the ammonia in the air of the nursery region.

These and other features, advantages, and objects of the present device will be further understood and appreciated by those skilled in the art upon studying the following specification, claims, and appended drawings.

BRIEF DESCRIPTION OF THE DRAWINGS

The invention will now be described with reference to the following drawings, in which.

DETAILED DESCRIPTION OF EMBODIMENTS

Implementations of the subject matter are demonstrated in exemplary representations herein. However, it is to be understood that the disclosed subject matter may assume various alternative packages and orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises a . . . " does not, without more constraints, preclude the existence of additional identical elements in the process, method, article, or apparatus that comprises the element.

Figure 1:
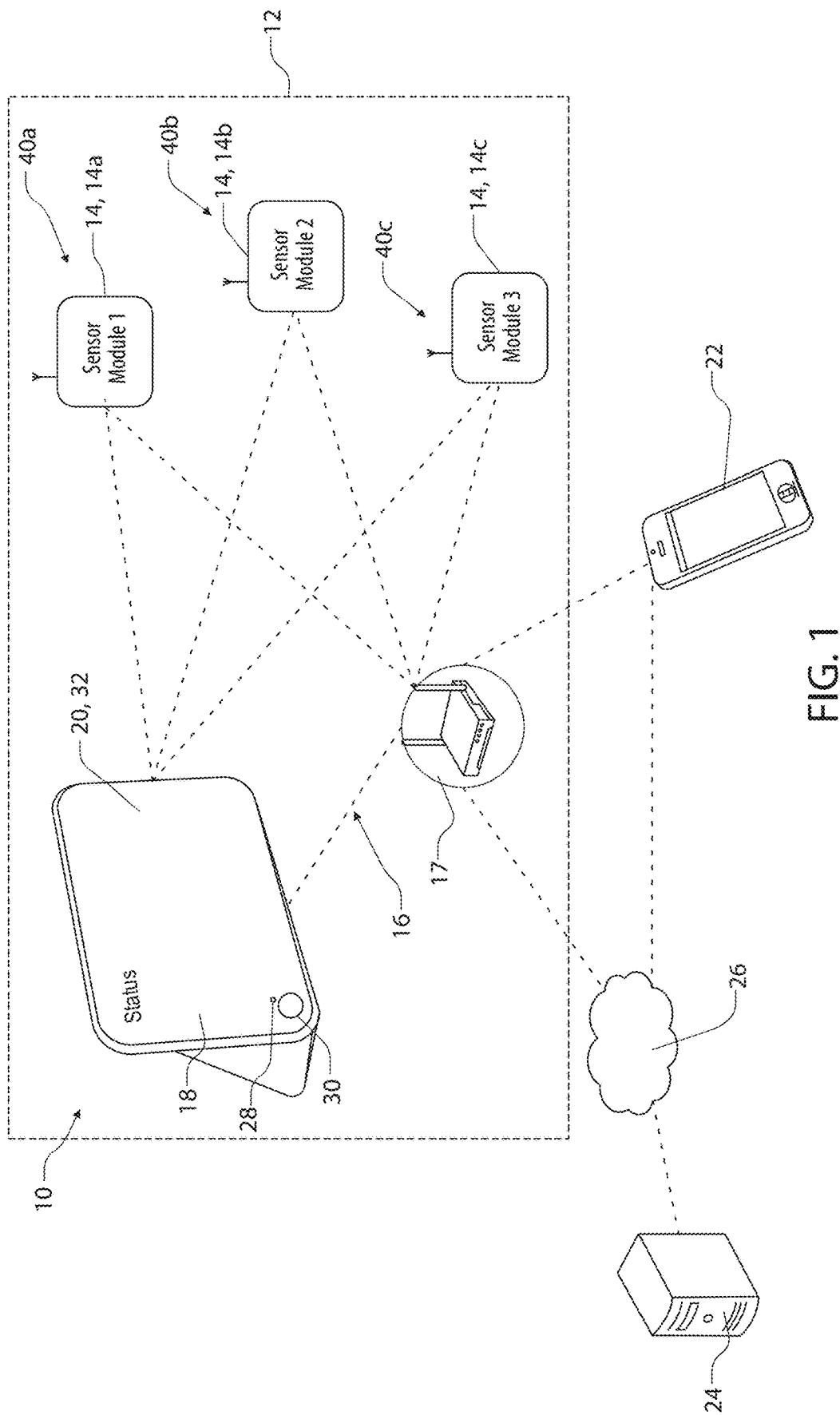
FIG. 1 is a block diagram demonstrating a monitoring system comprising a status hub.

Referring now to FIG. 1, reference numeral 10 generally designates a monitoring system for a building or home 12. The monitoring system 10 may comprise a plurality of sensor modules 14 that may be utilized to detect a condition of each of a plurality of zones or rooms in the building or home 12. In some examples, each of the sensor modules 14 may be configured to monitor particular environmental conditions and provide for various functions that may be configured to detect room or zone-specific conditions. The conditions may include a wide variety of temperature and environmental conditions that may be associated with the corresponding zone, room, or environment which a respective sensor module 14 is configured to monitor. As discussed herein, the sensor modules 14 comprise a garage module 14*a*, a kitchen module 14*b*, and a bedroom or nursery module 14*c*. However, additional sensor modules 14 may be utilized in coordination with the system 10 without departing from the spirit of the disclosure.

Each of the sensor modules 14 may be connected via a wireless communication network 16, which may utilize a reporting device (e.g. a wireless router 17 and/or a status hub 18), which may further comprise a status interface 20. The communication network 16 may be implemented by utilizing a variety of communication protocols configured to distribute data among various electronic devices. For example, the communication network 16 may comprise an IEEE 802.11 connection, and IEEE 802.15 connection, a Bluetooth® connection, a Wi-Fi connection, a WiMAX connection, cellular signal, a signal using Shared Wireless Access Protocol-Cord Access (SWAP-CA) protocol, or any other type of RF or wireless signal. An IEEE 802.15 connection includes any wireless personal area networks (WPAN), such as ZigBee, Z-Wave, Bluetooth®, UWB, and IrDA. In this configuration, the communication network 16 may provide for the sensor modules 14 to share and receive information from a mobile device 22, the status hub 18, and/or a remote server 24 or a cloud-based network via an internet connection 26.

The mobile device 22 may be in communication with the status hub 18 and/or the sensor modules 14 via the communication network 16. Accordingly, though discussed in reference to the status hub 18 and the status interface 20, the reporting device may be implemented as the mobile device 22 or various devices that may be in communication with the sensor modules 14. In this way, a user of the system 10 may flexibly access the status signals and various information captured via the sensor modules 14. Additionally, the mobile device 22 may be configured to send and/or receive audio messages such that the sensor modules 14 may further provide for two-way communication. As discussed herein, the mobile device 22 may correspond to various forms of mobile devices including, but not limited to, a smartphone, tablet, cellular telephone, laptop, computer, etc.

In order to provide for the two-way communication, the status hub 18, as well as one or more of the sensor modules 14, may comprise a microphone 28 and/or a speaker 30. In such embodiments, the system 10 may also be configured to control output prerecorded or generated audible warnings configured to communicate the nature of a condition or one or more warnings, instructions, and/or additional information to a user via the speaker 30 associated with each of the sensor modules 14 and the status hub 18. Accordingly, in response to the detection of one or more states or conditions detected in each of the zones or rooms where the sensor modules 14 and/or the status hub 18 are located, the system may output a status notification or alert identifying the detected state. Additionally, the system 10 may be configured to initiate an emergency communication (e.g. a telephonic communication) from the system 10 in response to the detection of a potentially hazardous chemical or environmental condition that may be detected by one or more of the sensor modules 14.

In addition to the microphone 28 and/or a speaker 30, one or more of the sensor modules 14 or the status hub 18 may comprise display screen 32. Additionally, the display screen 32 may serve as a touchscreen interface configured to receive inputs providing for the status interface 20 of the status hub 18. Though shown as a separate device, the status hub 18 may include or comprise one or more of the sensor modules 14 in a single, continuous package. Additionally, the multiple status hubs 18 may be implemented to improve access to the status of various aspects of the home 12 that are monitored via the sensor modules 14. Accordingly, the system 10 may provide for a convenient and flexible solution configured to monitor and communicate specific environmental, ambient, security, and/or status conditions of each of the monitored zones and the objects or lifeforms located in the zones as further discussed in the following detailed description.

Figure 2:
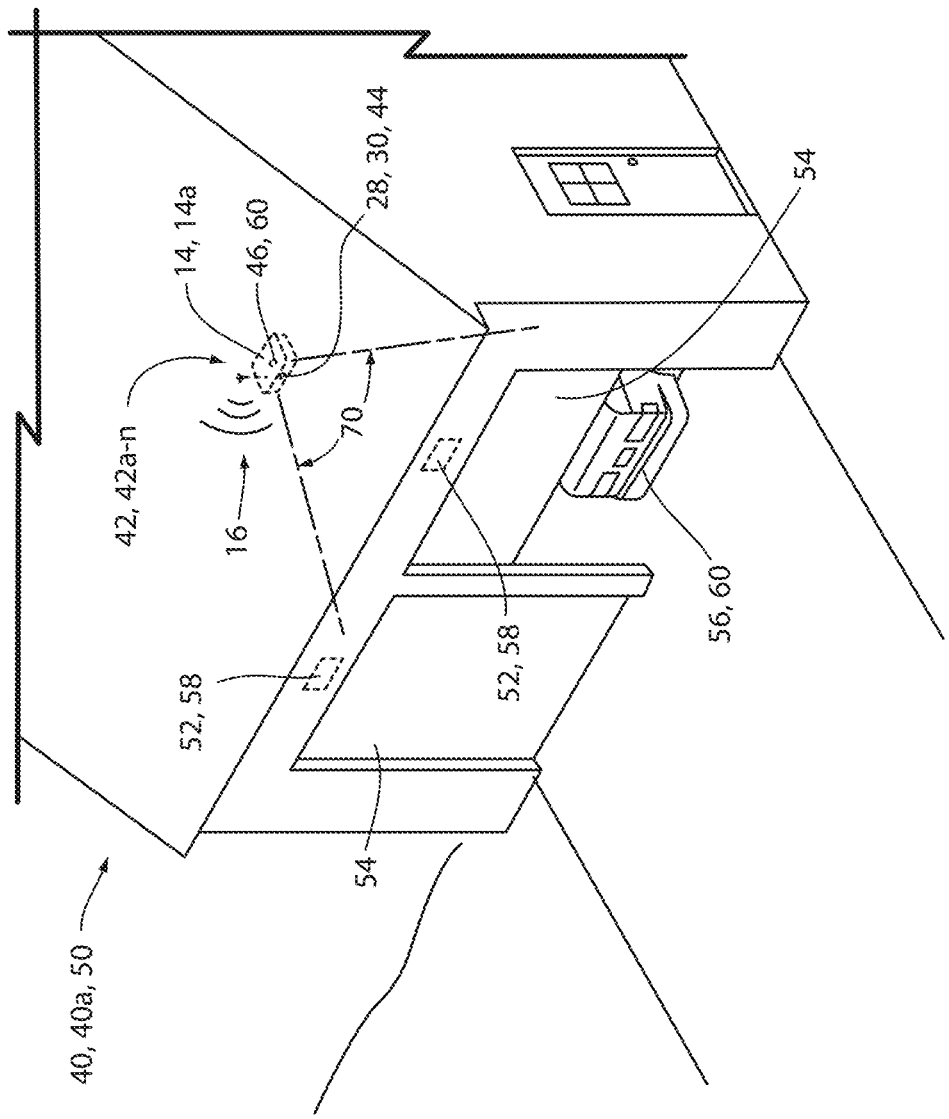
FIG. 2 is a projected view of a garage comprising a sensor module in communication with a monitoring system.
Figure 3:
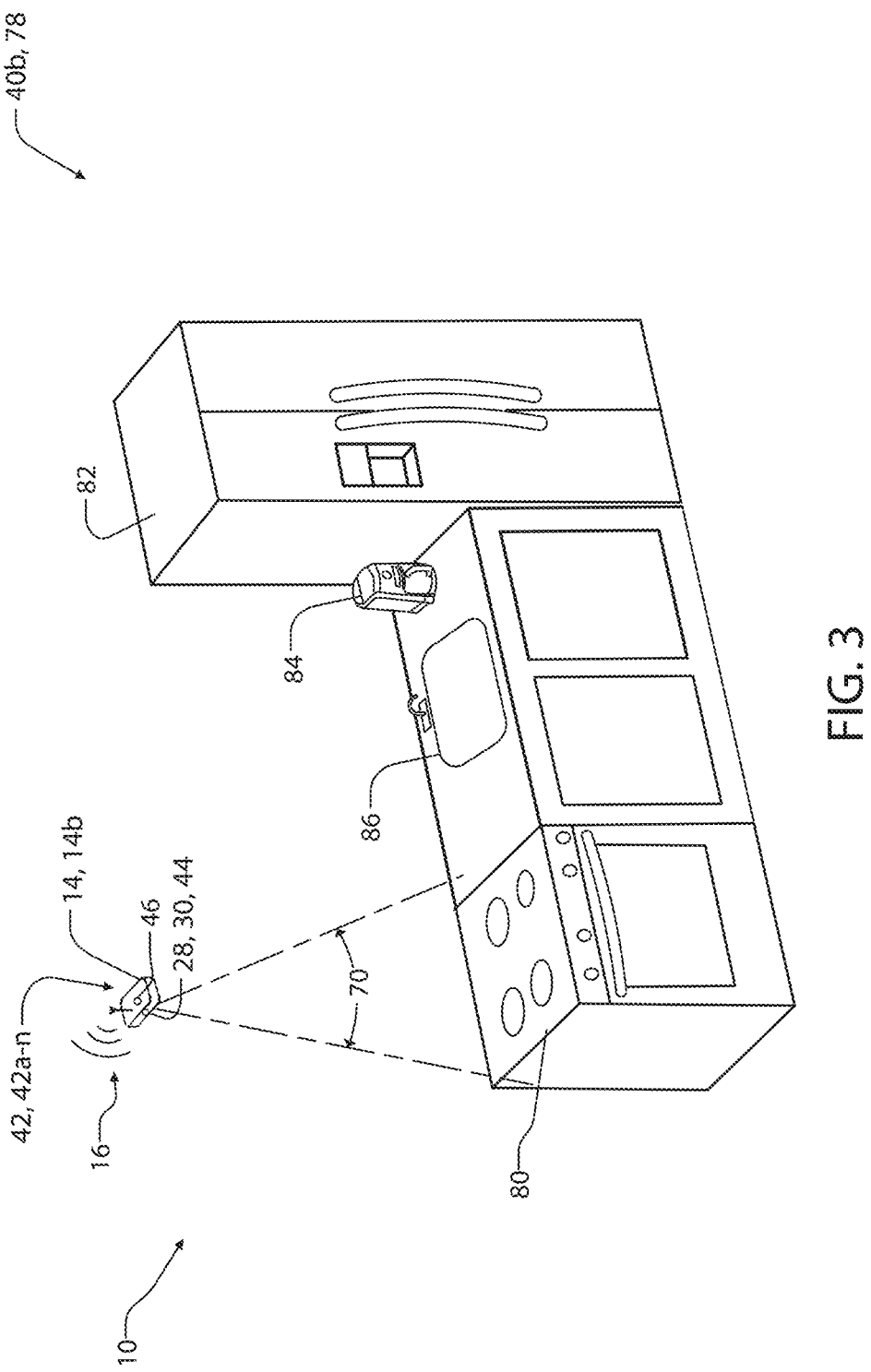
FIG. 3 is a projected view of a kitchen comprising a sensor module in communication with a monitoring system.
Figure 4:
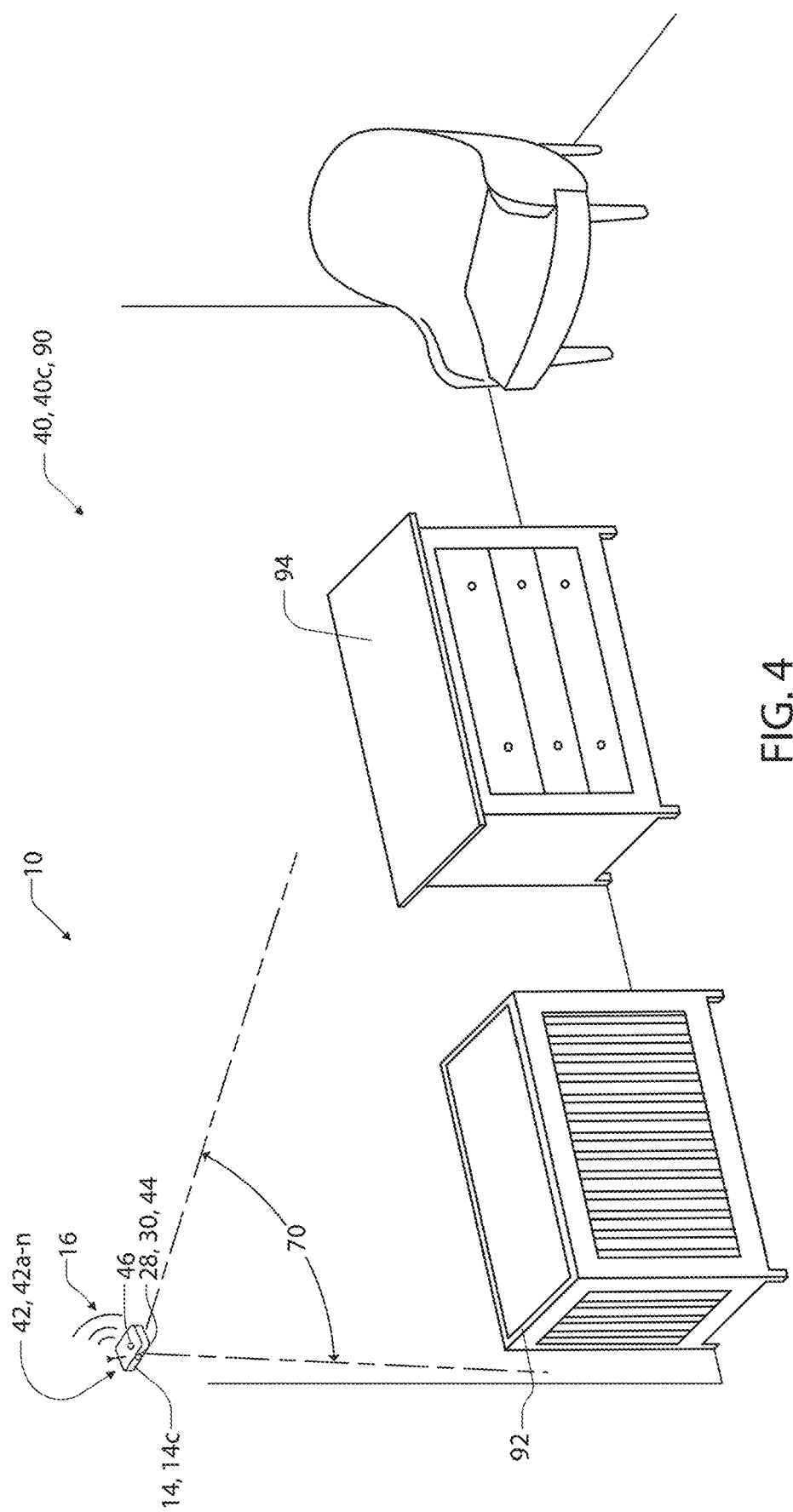
FIG. 4 is a projected view of a nursery comprising a sensor module in communication with a monitoring system.

Referring generally now to FIGS. 2-4, a plurality of zones 40a, 40b, and 40c are shown demonstrating exemplary operating environments for the garage module 14a, the kitchen module 14b, and the bedroom or nursery module 14c. As previously described, each of the modules 14 may comprise a specific array or suite of detection devices 42 and/or additional devices (e.g. peripheral devices, such as the microphone 28 and/or a speaker 30). For example, the sensor modules 14 may comprise a set or array of detection devices designed to track conditions and/or provide services or automated operations suited to each of the zones 40. For example, each of the modules 14 may comprise a variety of the detection devices 42, communication devices 44, indicators, lights 46, and various additional features that may be suited to the zone 40 in which the module 14 is configured to operate.

In various embodiments, the detection devices 42 may include, but are not limited to, an imaging device 42a, a vapor or air quality detection device 42b, moisture sensors 42c, a proximity sensor 42d, carbon monoxide sensor 42e, heat sensor 42f, thermometer 42g, humidity sensor 42h, vital sensors 42i, infrared temperature sensors 42j, a vehicle sensor 42k, barrier status sensor 42m, smoke detection device 42n, and/or various additional sensors that may be suited to the environments of the respective zones 40. In this way, each of the sensor modules 14 may provide for a wide variety of detection functions and features that may be associated with the zones 40. The following description provides for examples of the garage module 14a, the kitchen module 14b, and the bedroom or nursery module 14c in reference to FIGS. 2-4.

In various aspects, one or more of the detection devices 42 may be implemented with a chemical sensor or nanofiber chemical sensor. The nanofiber chemical sensor may be configured to sense various chemicals and compounds that may be present in the ambient air within the one or more compartments 14. In operation, each of the nanofiber chemical sensors may communicate with a processor configured to monitor changes in electrical characteristics for each of the nanofiber chemical sensors in the presence of the various airborne materials. Based on the combination of signals received from the nanofiber chemical sensor(s), the system 10 may identify the presence and concentration of one or more contaminants in one or more of the zones 40 or rooms.

The nanofibers used in the sensors may be synthesized with specific functional groups that can interact with specific airborne materials/vapors/particles. The nanofibers are deposited on an interdigitated electrode to form an electrode-nanofiber array. Interaction of the nanofibers with airborne materials changes the measured electrical characteristics of the nanofiber chemical sensor. An increase or decrease in the measured current or effective resistance of each of the nanofiber chemical sensors occurs as a result of interaction with these airborne material interactions. Examples of nanofiber chemical sensors are discussed in detail in U.S. Patent No. 10,962,493, entitled, "NANOFIBER SMOKE DETECTION CALIBRATION" filed Apr. 18, 2019, by David J. Cammenga; U.S. Patent Publication No. 2020/0080978 A1, entitled, "MULTIMODE PLATFORM FOR DETECTION OF COMPOUNDS" filed Sep. 17, 2019, by Ling Zhang; and U.S. Patent Publication No. 2018/0348129 A1, entitled, "NANOFIBRIL MATERIALS FOR HIGHLY SENSITIVE AND SELECTIVE SENSING OF AMINES" filed Nov. 21, 2017, by Ling Zhang, which are included herein by reference in their entirety.

Referring now to FIG. 2, an example of the garage module 14a is shown. The garage module 14a may comprise a plurality of detection devices 42 that may be suited to detect conditions that may be encountered in a garage 50. In the illustrated example, the garage 50 comprises at least one garage door opener 52 configured to open and close a garage door 54 to provide selective access to the garage 50. The garage door opener 52 may include an electronic receiver 58 configured to receive command in the form of wireless control signals from a remote control device (e.g. a dedicated garage door opener remote) and/or a programmable or trainable transmitter 60 that may be incorporated in the vehicle 56, the garage module 14a, and/or various modules or devices of or in communication with the system 10. As discussed herein, the trainable transmitter may correspond to a HOMELINK® system. Examples of trainable control systems and other similar systems are described in U.S. Pat. No. 9,819,498, entitled "SYSTEM AND METHOD FOR WIRELESS RE-PROGRAMMING OF MEMORY IN A COMMUNICATION SYSTEM," filed Aug. 21, 2012, by Chris H. Vuyst; and U.S. Pat. No. 8,384,513, entitled "TRANSMITTER AND METHOD FOR TRANSMITTING AN RF CONTROL SIGNAL," filed Jan. 3, 2006, by Todd R. Witkowski, which are included herein by reference in their entirety.

In order to monitor the garage 50, the garage module 14a, may be centrally mounted such that the detection devices 42 may detect conditions in the garage 50 that may be of interest and communicate such conditions to the status hub 18 and among the various devices (e.g. the mobile device 22) and modules 14 of the system 10. In an exemplary implementation, the garage module 14a may comprise a trainable transmitter 60, the imaging device 42a, the vapor or air quality detection device 42b, a proximity sensor 42d, carbon monoxide sensor 42e, heat sensor 42f, thermometer 42g, humidity sensor 42h, infrared temperature sensors 42j, a vehicle sensor 42k, barrier status sensor 42m, and/or a smoke detection device 42n. Additionally, the garage module 14a may comprise a light source 62, the microphone 28, and/or the speaker 30. In this configuration, the garage module 14a may be configured to detect a variety of conditions in the garage 50 and control the garage door opener 52 via an activation of the trainable transmitter 60. For example, the garage module 14a may be configured to control the garage door opener 52 to open the garage door 54 in response to a remote access request via the status hub 18 and/or the mobile device 22 or in response to an air quality condition or evacuation concern as identified by the detection devices 42 as discussed herein. Additionally, the garage module 14a may be configured to communicate a status to the status hub 18 and/or announce a status or condition of the garage 50 or any of the zones 40 of the sensor modules 14 in communication with the system 10.

In operation, the detection devices may each be configured to detect one or more conditions of interest in the garage 50. For example, the imaging device 42a may be implemented to detect motion and/or identify objects in the garage 50. Such detection may be implemented to identify a security status resulting from the detection of a person or animal in the garage 50 and/or identify a presence of the vehicle 56 based on the associated image data. Additionally, the vapor or air quality detection device 42b may be implemented to detect one or more air contaminants or chemicals in the air. Such detections may not only be utilized to identify air quality conditions but also an operating state of the vehicle 56 and to identify a fuel or fluid leak deposited on a floor or surface of the garage 50. The air quality may identify the presence of such contaminants and identify the nature of the contaminants based on the chemical composition of particles identified in the garage 50. Additionally, the air quality detection device 42b may be associated with a carbon monoxide sensor 42e. In this way, the garage module 14a may be configured to detect a variety of conditions in the garage 50. Further details air quality detection device 42b are discussed in reference to FIG. 5.

In some implementations, the garage module 14a may further comprise one or more detection devices 42 configured to detect conditions in the garage 50. For example, the heat sensor 42f or the thermometer 42g may be configured to detect increased heat levels that may be associated with a fire. Similarly, the smoke detection device 42n may be configured to detect smoke from a fire condition in the garage 50. The garage module 14a may further comprise a vehicle sensor 42k (e.g. an inductive sensor) to detect the presence of the vehicle 56 in the garage 50 as well as the barrier status sensor 42m (e.g. an inductive or optical sensor, momentary switch, etc.) to detect a closure status of the garage door 54. In some implementations, the garage module 14a may be configured to control the garage door 54 to open or prevent the garage door 54 from closing in response to a detection that the vehicle 56 is present in the garage and an engine is running. The determination of the vehicle 56 running may be determined by the garage module 14a, and more generally by the system 10, based on emissions detected via the detection devices (e.g. the air quality detection device 42b) or communications from a communication circuit in the vehicle 56.

In some implementations, the garage module 14a may be configured to detect the temperature and humidity of the garage 50 with the thermometer 42g and the humidity sensor 42h. Additionally, the garage module 14a may be configured to detect the temperature of one or more objects or surfaces of objects in the garage 50. For example, the garage module 14a may comprise one or more of the infrared temperature sensors 42j, which may be directed to a portion of the garage 50 where the vehicle 56 may commonly be parked. The garage module 14a may similarly or additionally comprise the imaging device 42a incorporating to an infrared imaging device and/or thermal imaging device. The thermal imaging device may correspond to a focal plane array (FPA) utilizing microbolometers as FPA sensors. In this way, the garage module 14a may be configured to detect and report temperature or fire related conditions in the garage 50.

As discussed herein, one or more of the sensor modules 14 may comprise a sensory window 70 (e.g. an imaging field of view, a detection range, etc.). Accordingly, a representative sensory window 70 is shown demonstrating the sensory window 70 aligned centrally within the garage 50 and configured to monitor a substantial portion of the garage 50 wherein the one or more vehicles 56 may be parked. Though a single garage module 14a is demonstrated in FIG. 2, the system 10 may comprise a plurality of modules 14 in each of the zones 40 in order to ensure coverage and responsive detection that may be scalable based on the proportions of each of the zones 40.

The trainable transmitter may be configured to control the garage door opener 52 (e.g., to issue a signal that causes the garage door opener 52 to open a garage door 54). The trainable transmitter may be trained using an original transmitter used to control garage door opener 52. For example, the original transmitter may be a hand-held garage door opener transmitter configured to transmit a garage door opener signal at a frequency, such as 355 Megahertz (MHz), wherein the activation signal has control data, which can be fixed code or cryptographically-encoded code (e.g., a rolling code). Accordingly, the system 10 may provide for the sensor module 14 to display instructions and/or warnings related to the detection of one or more states, events, chemicals, etc. that may be detected by the detection devices 42.

Referring now to FIG. 3, an example of the kitchen module 14b is shown in a kitchen 78 representing the second zone 40b. The kitchen module 14b may comprise a plurality of the detection devices 42 that may be suited to detect conditions that may be encountered near a range 80 (e.g. oven, cooktop, etc.), a refrigerator 82, a small appliance 84 (coffee maker, toaster, microwave, etc.), a dishwasher, and/or a sink 86. For example, the kitchen module 14b may comprise an imaging device 42a, a vapor or air quality detection device 42b (e.g. explosive gas detector), moisture sensors 42c, a carbon monoxide sensor 42e, heat sensor 42f, thermometer 42g, infrared temperature sensors 42j (e.g. flame or heat detection), smoke detection device 42n (e.g. an optical smoke detection device), and/or various additional sensors suited to the environment of the kitchen 78. Additionally, the kitchen module 14b may comprise the light source 62 (e.g. a motion or security light), the microphone 28, and/or the speaker 30. Though discussed in reference to the kitchen 78, the sensor module 14b may be similarly suited for placement in a utility room containing a washer, clothes dryer, slop sink, etc.

In operation, the imaging device 42a may be configured to detect a usage or occupancy of the kitchen 78. Such information may be implemented by the system 10 as an indication of the security status of the building or home 12. The system 10 may monitor the vapor or air quality detection device 42b to identify a variety of chemical compositions that may be detected in the kitchen 78. For example, the air quality detection device 42b may be configured to detect a gas leak (e.g. associated with the range 80), burning food products, chemical leaks or usage of household chemicals, and/or a contaminant odor that may be related to the sink 86 and/or a garbage or refuse receptacle. The system 10 may monitor the moisture sensors 42c to detect leaks related to the sink or refrigerator 82, which may be utilized to identify unexpected thawing events.

The smoke detection device 42n of the kitchen module 14b may be monitored by the system 10 to identify and/or report a fire or smoke-related events that may be associated with the range 80 and/or the small appliance 84. Similarly, the thermometer 42g and the infrared temperature sensor 42j may be configured to detect localized heating proximate to the kitchen module 14b and or high-temperature zones located in the sensory window 70 as previously discussed. In this way, the system 10 may utilize the kitchen module 14b to detect and report a variety of events or conditions that may be attributed to kitchen related appliances and related conditions in the home 12.

In some examples, the modules 14 (e.g., the kitchen module 14b) may be configured to report one or more alert conditions to the status hub 18 in response to the detection of a combination of conditions identified in the corresponding zone 40. In some instances, the system 10 may be configured to report a condition in each of the zones 40 in response to a time or duration of a detection as well as an occupancy of the zone 40 in which the activity is detected. For example, the system 10 may report a burning condition (e.g. odor associated with burning as detected by the air quality detection device 42b, smoke detection device 42n, etc.) if the condition is detected for a first predetermined time (e.g. 30 seconds, 2 minutes, 5 minutes, etc.) when the kitchen 78 is unoccupied as identified by the imaging device 42a. In an instance where the kitchen 78 or the corresponding zone 40 is occupied, the system 10 may report the condition if detected for a second predetermined period of time (e.g. 5 minutes, 15 minutes, 30 minutes, etc.). In some cases, the second predetermined time may exceed the first predetermined time, such that the notification when the zone 40 is occupied is not perceived as a nuisance. Though discussed in reference to the burning condition as detected by the kitchen module 14b, the notifications for each of the conditions detected by the system 10 may vary based on the occupancy, timing, and the combination of various other conditions that may be detected by the sensor modules 14 of system 10 as discussed herein. Also, though discussed in reference to the occupancy of each of the zones 40, the system 10 may similarly adjust the timing of notifications and alerts based on a zone being unoccupied for a predetermined period of time.

Referring now to FIG. 4, an example of the bedroom or nursery module 14c is shown in a nursery 90 representing the third zone 40c. The nursery module 14c may comprise a plurality of the detection devices 42 that may be suited to detect conditions that may be encountered near a crib 92, a changing table 94, a refuse container, etc. For example, the nursery module 14c may comprise the imaging device 42a, a vapor or air quality detection device 42b (e.g. ammonia sensor), a carbon monoxide sensor 42e, thermometer 42g, humidity sensor 42h, vital sensors 42i, a smoke detection device 42n, and/or various additional sensors that may be suited to the environments of the nursery 90.

The air quality detection device 42b (e.g. ammonia sensor) may be configured to detect urine or excrement in the nursery 90 that may be related to a soiled diaper. In response to such detections, the system 10 may be configured to receive one or more instructions to mute/silence or delay alerts for a selected or predetermined period of time. Muting or silencing the alerts may provide for period of time for a user (e.g., a parent or caretaker) to clean or remedy the source of the odor without consistent or repeated triggering of the detection. The silence or delay of the warning or alarm may be controlled by a user interface, which may be incorporated on the nursery module 14c and/or the status interface 20, which may be incorporated or used in conjunction with each of the modules 14a, 14b, etc. Accordingly, the system 10 may enable the user to control the activation of a temporary mute operation or delay of one or more of the alerts output from the nursery module 14c in response to a variety of user inputs including but not limited to an input to a pushbutton or touchscreen received by the status interface 20, a voice instruction received via the microphone 28, and/or a gesture recognized by the imaging device 42a.

In addition to the alert output from the nursery module 14c, the system 10 may additionally be configured to control one or more connected devices (e.g., a fan, air purifier, air freshener, etc.) in response to the detection of the urine or excrement. Such control instructions may be configured by an operator of the system 10, such that the nursery module 14c and/or any of the sensor modules 14 may be configured to control a connected device (e.g., smart device) in response to the detection of one or more conditions in each of the rooms or zones monitored by the system 10. Such associations or automated controls may be set up via the status interface 20 and/or the mobile device 22 in communication with the system 10.

The vital sensors 42i may correspond to a microwave Doppler sensor, millimeter-wave sensor, conventional imaging device, and/or range imagery device configured to detect the behavior of an occupant of one or more zones 40 of the system 10. For example, the vital sensor 42i may correspond to a microwave Doppler sensor directed toward a crib 92 of the nursery 90 and configured to detect the heartbeat and heart rate of a baby in the crib 92. More generally, the sensory window 70 of the vital sensor 42i may be directed to cover a mattress in the crib 92, such that the nursery module 14c may detect and report the heart rate, movement, and various activities of the baby or subject of the sensor data. Additionally, the module 14c and the system 10 may be configured to output status indications in response to the heart rate varying from a user-selected or preconfigured range of heart rates. In this configuration, the system 10 may provide for monitoring and alerts output via the sensor modules 14, the status hub 18, and/or the mobile device 22 to alert the user to a variety of conditions in the nursery 90.

In some aspects, the nursery module 14c may further be configured to detect carbon monoxide levels at low concentrations. For example, the level of carbon monoxide in one or more of the zones 40 may be detected at levels exceeding 6-10 ppm. Accordingly, the carbon monoxide sensor 42e may be configured to communicate the level of carbon monoxide, such that the modules 14 (e.g. the nursery module 14c, kitchen module 14b, etc.) may communicate an alert to the status hub 18 in response to the detection of a level of carbon monoxide exceeding a predetermined level (e.g. greater than 20 ppm, greater than 40 ppm, etc.) depending on the sensitivity of the corresponding zone 40 to the presence of the carbon monoxide. Accordingly, the system 10 may selectively communicate one or more alerts in response to the detection of the carbon monoxide at different levels in each of the zones 40.

Additionally, the nursery module 14c may comprise the light source 62 (e.g. a motion or security light), the microphone 28, and/or the speaker 30. The light source may be configured as a task light and/or night light. The microphone 28 and speaker 30 may be configured to provide for a monitoring operation of a baby or individual in the nursery 90 as well as two-way communication via the mobile device 22 and/or the status hub 18.

In general reference to FIGS. 2-4, the imaging device 42a may correspond to a charge-coupled device (CCD) and the active-pixel sensor (CMOS sensor) configured to detect a usage or occupancy of each of the zones 40. Such information may be implemented by the system 10 as an indication of the security status of the building or home 12. Additionally, the system 10 may monitor the vapor or air quality detection device 42b to identify a variety of chemical compositions that may be detected in or among the zones 40. In this way, the system 10 may be configured to identify a location of a security event or environmental condition in one of the zones 40 and communicate the location of the condition via each of the sensor modules 14, the status hub 18, and/or the mobile device 22.

The imaging device 42a may be implemented in a variety of ways. For example, in an exemplary embodiment, the imaging device 42a may comprise at least one image sensor, which may be in communication with one or more image processors and/or a memory configured to complete the various processing steps for image data captured in the sensory window 70. The image processors may be integrated with or separately provided from a controller of the system 10. As discussed further in reference to FIG. 6, the imaging device 42a may be in communication with a communication circuit, which may be configured to communicate the image data to a remote server or device (e.g. a mobile device) for processing, review, and/or communication in relation to one or more notifications. Accordingly, the sensor module 14, the status hub 18, and/or the remote server 24 may be configured to process the image data captured by each of the imaging devices 42a discussed herein to complete various image processing and identification steps discussed herein.

In some examples, the imaging device 42a may correspond to a plurality of imaging devices or stereoscopic imaging devices. The imaging device 42a may also correspond to an infrared imaging device, thermal imaging device, or a combination of thermal and conventional imaging devices. The thermal imaging device may correspond to a focal plane array (FPA) utilizing microbolometers as FPA sensors. Accordingly, the image data captured by the system 10 may comprise thermal image data and/or conventional image data in the visible light spectrum. In this way, imaging device 42a may be configured to detect changes in the image data by scanning each of the zones 40 in a variety of different wavelength of light (e.g. ultraviolet [UV], infrared [IR], etc.) and compare the image data to identify a variety of conditions.

Figure 5:
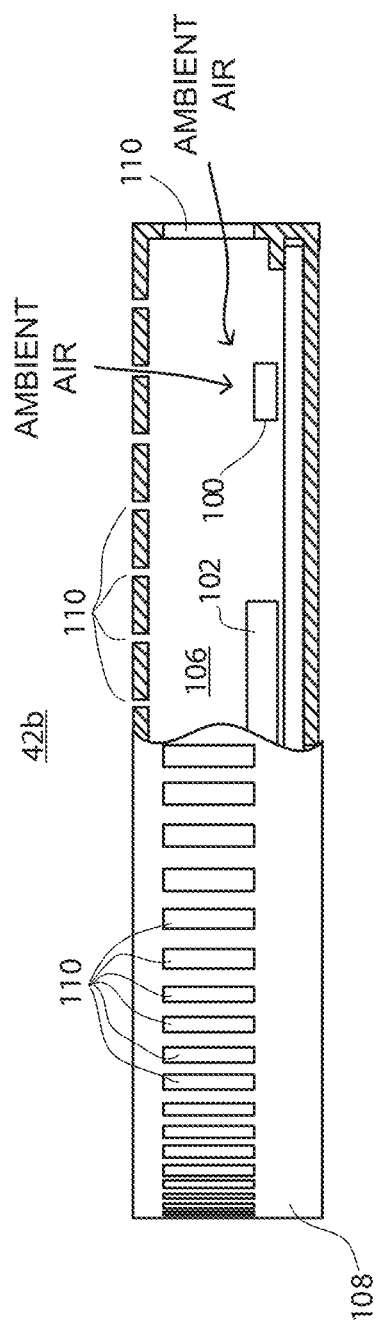
FIG. 5 is a schematic diagram of a vapor sensor that may be implemented in a sensor module.

Referring now to FIG. 5, an exemplary schematic diagram of the air quality detection device 42b is shown. The air quality detection device 42b may be configured to identify a type and/or concentration of various chemicals in each of the zones 40 discussed herein. In various aspects, the air quality detection device 42b may correspond to a variety of sensory devices. For example, the air quality detection device 42b may be implemented by a variety of devices including, but not limited to, electrochemical sensors, amperometric gas sensors, carbon monoxide sensors, catalytic bead sensors, thermal conductivity sensors, metal oxide sensors (MOS), infrared (IR) sensors, photoionization detectors (PID), etc. Such sensors may vary in application and, therefore, may be implemented in various combinations to achieve the identification and detection of various chemicals and contaminants that may be present in the rooms or detection zones as discussed herein. Though specific examples are discussed herein, the air quality detection device 42b may be implemented by similar sensors or developing sensory technologies without departing from the spirit of the disclosure.

In some embodiments, the air quality detection device 42b may comprise at least one nanofiber chemical sensor 100. The nanofiber chemical sensor 100 may be configured to sense various chemicals and compounds that may be present in the ambient air within the zones 40. In some aspects, the at least one nanofiber chemical sensor 100 may comprise a plurality of nanofiber chemical sensors. In operation, each of the one or more nanofiber chemical sensors 100 may be in communication with a processor 102, which may be configured to monitor changes in electrical characteristics for each of the nanofiber chemical sensors 100 in the presence of the various airborne materials. Based on the combination of signals received from the at least one nanofiber chemical sensor 100, the processor 102 may be configured to identify the presence of one or more contaminants in the zones 40.

The nanofibers used in the sensors 100 may be synthesized with specific functional groups that can interact with airborne materials/vapors/particles. The nanofibers are deposited on an interdigitated electrode to form an electrode-nanofiber array. Interaction of the nanofibers with airborne materials changes the measured electrical characteristics of the nanofiber chemical sensor 100. An increase or decrease in the measured current or effective resistance of each of the nanofiber chemical sensors occurs as a result of these airborne material interactions.

Nanofibers of each of the sensors 100 with different functional groups have a different response to the same airborne material. By using the plurality of nanofiber chemical sensors 100 in an array, an identifying response signature can be established by the processor 102 for each of a plurality of airborne materials. Accordingly, based on the electrical signals communicated from the array, the processor 102 may be configured to detect a variety of conditions that may exist in the home 12 and/or the zones 40. The nanofibers of the sensors 100 may have a proportionately large three-dimensional surface area that is resistant to particulate fouling. In various aspects, the processor 102 may be configured to identify a variety of contaminants in the zones 40 in response to the particular contaminant or family of contaminants identified by the air quality detection device 42b.

In various aspects, the air quality detection device 42b may be configured to identify a variety of chemicals present in the passenger compartment and/or proximate to the corresponding sensor module 14. Chemicals and compounds that may be detected by the device 42b may be trained or programmed based on electrical signatures received by the processor 102 in response to the presence of the chemicals. Examples of chemicals that may be identified and/or detected may include, but are not limited to, Benzaldehyde, Hexane, Acetone, Ethanol, Diesel Fuel, Nitrobenzene, and Formaldehyde. Some examples of explosives and chemical agents that may be detected may include Nitromethane, DNT (Dinitrotoluene), TNT (Trinitrotoluene), ANFO (Ammonium Nitrate Fuel Oil), Ammonium Nitrate, PETN (may detect taggant), RDX (may detect taggant), TATP (Triacetone Triperoxide), H2O2 (Hydrogen Peroxide), TEP (Triethylphosphate), DMMP (Dimethyl methylphosphonate), 2-Chloroethyl ethyl sulfide, Triphosgene, and Methyl Salicylate. Some examples of toxic chemicals that may be detected by the air quality detection device 42b may include, but are not limited to, Chlorine Gas, Ammonia, Hydrogen Peroxide, Sulfur Dioxide, Hydrochloric Acid, TEP (Triethyl Phosphate), Phosphine, Hydrogen Cyanide, Arsine, and Formaldehyde. In some examples, the detection device may also be configured to detect one or more chemicals commonly found in consumer foods and/or goods including, but not limited to, Trichloroanisole, Melamine, Trimethylamine, Limonene, Pinene, Linalyl acetate, Menthol, Menthone, and Linalool. The device 42b may additionally be configured to detect various amines including, but not limited to, N-Methylphenethylam-lamine, Phenethylamine, Methylamine, Aniline, Triethylamine, and Diethylamine. Accordingly, based on the detection of each of the chemicals detected by the device 42b, the sensor module 14 may provide a corresponding response, which may update a status indication on the status hub 18, control the garage door opener 52, control a light or alarm notification, update a security status, relay an emergency notification, etc.

The chemical sensors 100 of the air quality detection device 42b may be arranged in any manner and may be disposed in an inner chamber 106 of a housing 108 having a plurality of air vents 110. The air vents 110 may provide for ambient and/or forced air to flow into the inner chamber 106. In this configuration, updated samples of the air present in the zones 40 may flow passed the chemical sensors 100 providing consistently updated monitoring of the chemical particulates present in the air. In various implementations, the air vents 110 may be large enough and/or numerous enough to allow the ambient air to flow into the inner chamber 106 without restriction. A processor 102 of the air quality detection device 42b may be in communication with the system 10 via a wired and/or wireless connection.

Common chemicals and corresponding odors that may be detected by the device 42b in each of the modules 14 may vary widely. For example, the device 42b may be configured to identify a variety of odors including, but not limited to, perfumes, feces, fish, skunk, pet odor, decaying biological material, methane, hydrogen sulfide, body odor (body-related bacterial odor), smoke, alcohol, bodily fluids, vomit, etc. Some of these odors may relate to comfort issues while others could present health issues to one or more users or occupants of one or more of the zones 40.

Additionally, the air quality detection device 42b may be configured to detect and identify a variety of chemicals that may generally be considered dangerous which may or may not cause a significant odor. Examples of such chemicals or sources of such chemicals may be allergens including, but not limited to, peanuts, soy, perfumes, smog, etc. Additional examples of chemical or sources of such chemicals may include, but are not limited to, explosives, gun powder, accelerants, carbon dioxide, carbon monoxide, volatile organic compounds (VOCs), drugs (e.g. methamphetamine, alcohol), smog, smoke, exhaust, etc. In response to the detection of such chemicals, the system 10 may respond in different ways, particularly in comparison to the detection of chemicals that may not be dangerous in relation to the occupancy of the zones.

Figure 6:
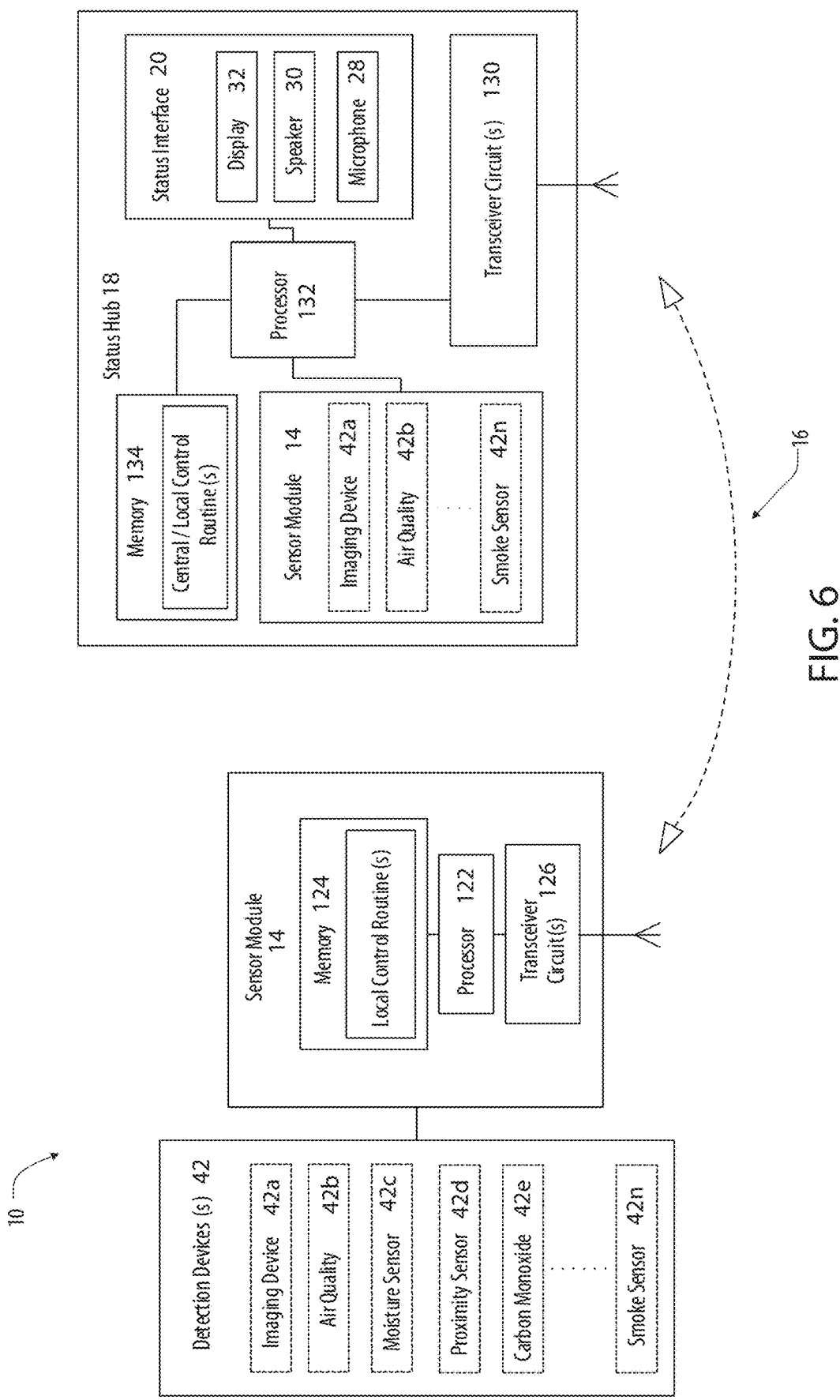
FIG. 6 is a block diagram of a sensor module in communication with a status hub as discussed herein.

Referring now to FIG. 6, a block diagram of the system 10 comprising the sensor module(s) 14 and the status hub 18. In FIG. 6, the sensor module 14 of the system 10 is shown in communication with each of the detection devices 42a-42n, etc. The sensor module 14 may comprise a processor 122 having one or more circuits configured to control various operations of the system 10. The processor 122 may be in communication with a memory 124 configured to store instructions to control operations of the detection devices 42 and control various aspects of the system 10 in response thereto. For example, the sensor module 14 may be configured to store one or more control responses configured to control various peripherals or status notifications of the system 10 in response to the status of each of the detection devices 42 and the corresponding zone 40.

In some embodiments, the status hub 18 may further comprise one or more communication circuits 126 configured to communicate via a communication network 16. Accordingly, the system 10 may be in communication with a remote server 24 and/or a mobile device 22 via the communication network 16. The communication network 16 may comprise one or more wireless or wired network interfaces or communication protocols. As discussed herein, wireless communication protocols may operate in accordance with communication standards including, but not limited to, the Institute of Electrical and Electronic Engineering (IEEE) 802.11 (e.g., WiFi™); Bluetooth®; advanced mobile phone services (AMPS); digital AMPS; global system for mobile communications (GSM); code division multiple access (CDMA); Long Term Evolution (LTE or 4G LTE); local multipoint distribution systems (LMDS); multi-channel-multi-point distribution systems (MMDS); RFID; and/or variations thereof. In this configuration, the sensor module 14 may be configured to send an alert or message to the mobile device 22 and/or the remote server 24 identifying a detection of a condition in the home 12 and a corresponding zone 40 of the detection. The alert or message may correspond to a text message, data message, email, alert via an application operating on the mobile device 22, etc.

As discussed herein the status hub 18 may also comprise a transceiver circuit 130 that may be in communication with the communication network 16, the remote server 24, and/or the mobile device 22. The status hub 18 may comprise a processor 132 in communication with a memory 134. The processor 132 may correspond to one or more microprocessors and/or control circuits configured to process instructions that may be stored in the memory 134. In an exemplary embodiment, the processor 132 may be configured to access and process instructions incorporated in a sensor control module, which may be stored in the memory 134. In this way, the processor 132 may be configured to process various computational tasks that may be associated with selecting and communicating the various modes, alerts, status indications, and notifications as discussed herein. Such alerts may be communicated via each of the sensor modules 14 as well as the status interface 20, which may comprise the microphone 28, the speaker 30, and a display screen as well as one or more of the sensor modules 14 integrated into a housing for use in one or more of the zones 40.

Though described generically as processors, each of the processors provided herein may correspond to various forms of application-specific integrated circuits (ASICS), digital-signal-processors (DSPs), a group of processing components, and/or other suitable electronic processing components. The memory devices may correspond to one or more devices (e.g. RAM, ROM, flash memory, hard disk storage, etc.) for storing data and/or computer code that may be utilized to facilitate the various processes described herein. It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only.

Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents.

What is claimed is:

1. A multi-zone monitoring system comprising:
   a plurality of sensor modules configured to monitor conditions in a plurality of detection zones, wherein the sensor modules comprise a combination of detection devices configured to detect different conditions based on a designated zone of each sensor module, wherein the plurality of sensor modules comprises:
   a kitchen sensor module configured to detect conditions in a kitchen region, wherein the kitchen sensor module comprises an air quality detection device configured to detect at least one of a flammable gas presence, a chemical leak, and a burning food product; and
   a kitchen occupancy sensor configured to detect an occupancy of the kitchen region, wherein a controller of the monitoring system is configured to control an alarm in response to the detection of the burning food product in combination with the occupancy; and
   a reporting device in communication with each of the sensor modules, wherein the reporting device is configured to report the status of each of the detection zones based on indications communicated via the detection devices in the corresponding detection zone.

2. The system according to claim 1, wherein the reporting device corresponds to at least one of a mobile device and a status hub in communication with each of the sensor modules via a wireless network.

3. The system according to claim 1, wherein the detection zones correspond to rooms in a building or home.

4. The system according to claim 1, wherein the plurality of sensor modules comprises a garage sensor module configured to detect conditions in a garage detection zone, wherein the garage sensor module is configured to detect and control a status of a garage door in the garage detection zone.

5. The system according to claim 4, wherein the garage sensor module comprises at least one of an air quality sensor and a vehicle sensor configured to detect a presence of a vehicle in the garage detection zone and detect an active operating condition of the vehicle.

6. The system according to claim 5, wherein a controller of the monitoring system is configured to control a garage door position in response to the active operation of the vehicle.

7. The system according to claim 4, wherein the garage sensor module is configured to detect a garage door position of a garage door and communicate the status of the garage door position to the reporting device.

8. The system according to claim 1, wherein the plurality of sensor modules comprises a nursery sensor module configured to detect conditions in a nursery region, wherein the nursery sensor module is configured to detect a heart condition associated with a person in the nursery region via a microwave sensor.

9. The system according to claim 8, wherein the nursery sensor module comprises an ammonia sensor configured to detect ammonia in the air of the nursery region.

10. The system according to claim 9, wherein the reporting device is configured to output a urine or excrement notification in response to the detection of the ammonia in the air of the nursery region.

11. The system according to claim 1, wherein the reporting device further comprises a microphone and a speaker forming a reporting communication interface, and at least one of the sensor modules comprises a sensor microphone and a sensor speaker forming a sensor communication interface.

12. The system according to claim 11, wherein the reporting communication interface and the sensor communication interface provide for two-way audio communication between the reporting device and the at least one sensor.

13. The system according to claim 1, wherein the reporting device comprises a display comprising a touchscreen interface, wherein the display is configured to display a status of each of the sensor modules.

14. A multi-zone monitoring system comprising:
    a plurality of sensor modules configured to monitor conditions in a plurality of detection zones, wherein the sensor modules comprise a combination of detection devices configured to detect different conditions based on a designated zone of each sensor module, wherein the detection devices comprise:

a kitchen sensor module configured to detect conditions in a kitchen region, wherein the kitchen sensor module is configured to detect a burning food associated with a stove or cooktop; and an occupancy sensor configured to detect an occupancy of the kitchen region, wherein a controller of the monitoring system is configured to control an alarm in response to the detection indication from the kitchen sensor module in combination with an indication of the occupancy; and wherein the plurality of sensor modules is in communication with a reporting device in communication with each of the sensor modules, and wherein the reporting device is configured to report the status of each of the detection zones based on indications communicated via the detection devices in the corresponding detection zone.

15. The system according to claim 14, wherein the kitchen sensor module comprises an air quality detection device configured to detect at least one of a flammable gas presence and a chemical presence.

16. The system according to claim 14, wherein the kitchen sensor is configured to detect a garbage odor and in response to the garbage odor, output a notification to remove or replace a garbage bag.

17. A multi-zone monitoring system comprising:
a plurality of sensor modules configured to monitor conditions in a plurality of detection zones, wherein the sensor modules comprise a combination of detection devices configured to detect different conditions based on a designated zone of each sensor module, wherein the plurality of sensor modules comprises:
a nursery sensor module configured to detect conditions in a nursery region, wherein the nursery sensor module comprises an ammonia sensor configured to detect ammonia in the air of the nursery region; and
an occupancy sensor configured to detect an occupancy of the nursery region, wherein a controller of the monitoring system is configured to control an alarm in response to the detection indication from the nursery sensor module in combination with an indication of the occupancy; and
wherein the plurality of sensor modules is in communication with a reporting device, wherein the reporting device is configured to report the status of each of the detection zones based on indications communicated via the detection devices in the corresponding detection zone, and wherein the reporting device is configured to output a urine or excrement notification in response to the detection of the ammonia in the air of the nursery region.

* * * * *